(12) United States Patent
Xiao et al.

(10) Patent No.: US 8,502,499 B2
(45) Date of Patent: Aug. 6, 2013

(54) CHARGING DEVICE FOR ELECTRIC DRIVABLE VEHICLE

(76) Inventors: Xiaofeng Xiao, Shenzhen (CN); Li Zhan, Shenzhen (CN); Ye Yuan, Shenzhen (CN)

(*) Notice: Subject to any disclaimer, the term of this patent is extended or adjusted under 35 U.S.C. 154(b) by 213 days.

(21) Appl. No.: 13/131,168

(22) PCT Filed: Nov. 23, 2009

(86) PCT No.: PCT/CN2009/075008
§ 371 (c)(1),
(2), (4) Date: May 25, 2011

(87) PCT Pub. No.: WO2010/072109
PCT Pub. Date: Jul. 1, 2010

(65) Prior Publication Data
US 2011/0260684 A1 Oct. 27, 2011

(30) Foreign Application Priority Data
Dec. 25, 2008 (CN) .......................... 2008 1 0207703

(51) Int. Cl.
*H02J 7/00* (2006.01)
*B60K 1/00* (2006.01)

(52) U.S. Cl.
USPC .......... 320/109; 320/108; 320/107; 180/65.1; 180/65.21; 180/65.29; 439/310; 439/34; 307/10.6; 307/46; 307/48; 307/10.1

(58) Field of Classification Search
USPC .......................................................... 320/109
See application file for complete search history.

(56) References Cited

U.S. PATENT DOCUMENTS

| | | | |
|---|---|---|---|
| 4,902,956 A * | 2/1990 | Sloan | 320/135 |
| 5,433,623 A | 7/1995 | Wakata et al. | |
| 5,614,808 A * | 3/1997 | Konoya et al. | 320/109 |
| 5,764,469 A * | 6/1998 | Slepian et al. | 361/92 |
| 5,977,652 A * | 11/1999 | Frey et al. | 307/10.1 |
| 6,371,768 B1 * | 4/2002 | Neblett et al. | 439/34 |
| 2003/0132042 A1 * | 7/2003 | Beihoff et al. | 180/65.1 |
| 2003/0210014 A1 * | 11/2003 | Jabaji et al. | 320/104 |
| 2007/0247106 A1 * | 10/2007 | Kawahara et al. | 320/104 |

FOREIGN PATENT DOCUMENTS
CN 101188319 5/2008

OTHER PUBLICATIONS
International Search Report for International Application No. PCT/CN2009/075088 dated Nov. 23, 2009.
Written Opinion of the International Searching Authority for International Application No. PCT/CN2009/075088 dated Nov. 23, 2009.

* cited by examiner

*Primary Examiner* — Yalkew Fantu
(74) *Attorney, Agent, or Firm* — Alston & Bird LLP

(57) ABSTRACT

A charging device for an electrically-drivable vehicle comprises a power-supply connector (100), a power-receiving connector (200), a safety-charging-signal-generating unit provided in the charging device, a CAN control module receiving a safety-charging signal generated by the safety-charging-signal-generating unit. The charging device may be configured to be chargeable to the electrically-drivable vehicle when the charging terminal and the charging-terminal-accommodating chamber are connected to each other. The power-supply connector and the power-receiving connector are engaged with the CAN module detecting the safety-charging signal. The personal safety during maintenance or other unexpected accidents is enhanced.

13 Claims, 4 Drawing Sheets

CHARGING DEVICE FOR ELECTRIC DRIVABLE VEHICLE

CROSS REFERENCE TO RELATED APPLICATION(S)

This application claims the benefit of Chinese Patent Application No. 2008-10227193.9, filed on Nov. 25, 2009, the content of which is incorporated herein in its entirety.

TECHNOLOGICAL FIELD

Example embodiments of the present invention relate to a charging device for an electrically-drivable vehicle, especially to a charging device for an electrically-drivable vehicle such as a pure electric vehicle, a hybrid power vehicle, etc.

BACKGROUND

A charging device for an electrically-drivable vehicle is a connection member between an energy storage device of the electrically-drivable vehicle and a charging apparatus used to charge the electrically-drivable vehicle. The function of such a charging device relates to forming a charging electric path between the energy storage device and the charging apparatus to supply power to the vehicle. Meanwhile, the charging device should ensure the safety of its operator as well as provide operational convenience.

One typical charging device for a pure-electric vehicle such as an electrically-drivable vehicle includes a charging gun. Presently, in order to protect personnel safety, the charging gun has locking and safety devices. The locking device is a mechanical one, and the safety device is controlled by a mechanical-contact safety terminal. Further, to avoid liquid flowing into the charging device, a sealing device is provided in the charging device. However, there is a disadvantage for this type of charging device that the mechanical safety device may be conducted during maintenance or other unexpected movement, consequently an on-board main relay is engaged, which may bring injuries accidentally. U.S. Pat. No. 5,820,395 to Shigemi Hashizawa, discloses a "Charging Connector for Electric Vehicle." However, when this charging connector is used to charge an electric vehicle with high electric current, the mechanical-contact safety terminal itself can not avoid the conducting of the charging circuit during maintenance or some unexpected movement, which may bring about a security risk for an operator. Namely, the safety device used in the charging connector is a mechanical terminal, and a charging path or circuit is formed when terminals at two ends of the charging connector are engaged with each other. However, the personal injury caused by the engagement of the on-board main relays can not be avoided during the intentional engagement whereas plugs in the charging connectors are not connected with each other, mainly caused by the large current during the charging process of the electric vehicle.

SUMMARY

In viewing of the foregoing background, example embodiments of the present invention provide a charging device that uses a double safety structure combining a mechanical safety structure with a CAN (Controlled Area Network) module to avoid latent safety accidents caused by accidental events, misoperation or the like.

According to an example embodiment of the present invention, a charging device for an electrically-drivable vehicle is provided, which may comprise a power-supply connector provided on a power-supply end, the power-supply connector being formed with a charging terminal or a charging-terminal-accommodating chamber, a power-receiving connector configured at a power-receiving end, the power-receiving connector being formed with the other of the charging terminal or the charging-terminal-accommodating chamber, a safety-charging-signal-generating unit provided in the charging device, and a CAN control module receiving a safety-charging signal generated by the safety-charging-signal-generating unit. The charging device may be configured to be chargeable to the electrically-drivable vehicle when the charging terminal and the charging-terminal-accommodating chamber may be connected to each other, the power-supply connector and the power-receiving connector may be engaged with the CAN module detecting the safety-charging signal.

From above, the electrically-drivable vehicle may be charged by the charging device according to an example embodiment of the present invention, only when the charging terminal is connected with the charging-terminal-accommodating chamber, the power-supply connector is connected with the power-receiving connector, and the CAN control module detects the safety-charging signals. Thus, a double or duo-safety charging structure is provided by the combination of a mechanical conductive structure and a CAN protection loop, which can avoid the safety risk caused by the accidental conduction of the mechanical conductive structure.

According to above example embodiment of the present invention, in addition to a mechanical terminal conductive structure, a CAN control module may be incorporated for detecting if the safety-signal terminal may be engaged and the CAN terminal may have been inserted completely. This can avoid the hurt of the over-current caused by the accidents to the operator.

The additional aspect and the advantages of example embodiments of the present invention will be disclosed in below description, some of them will become clear through the description, or get known through the practice.

BRIEF DESCRIPTION OF THE DRAWINGS

Figure 1:
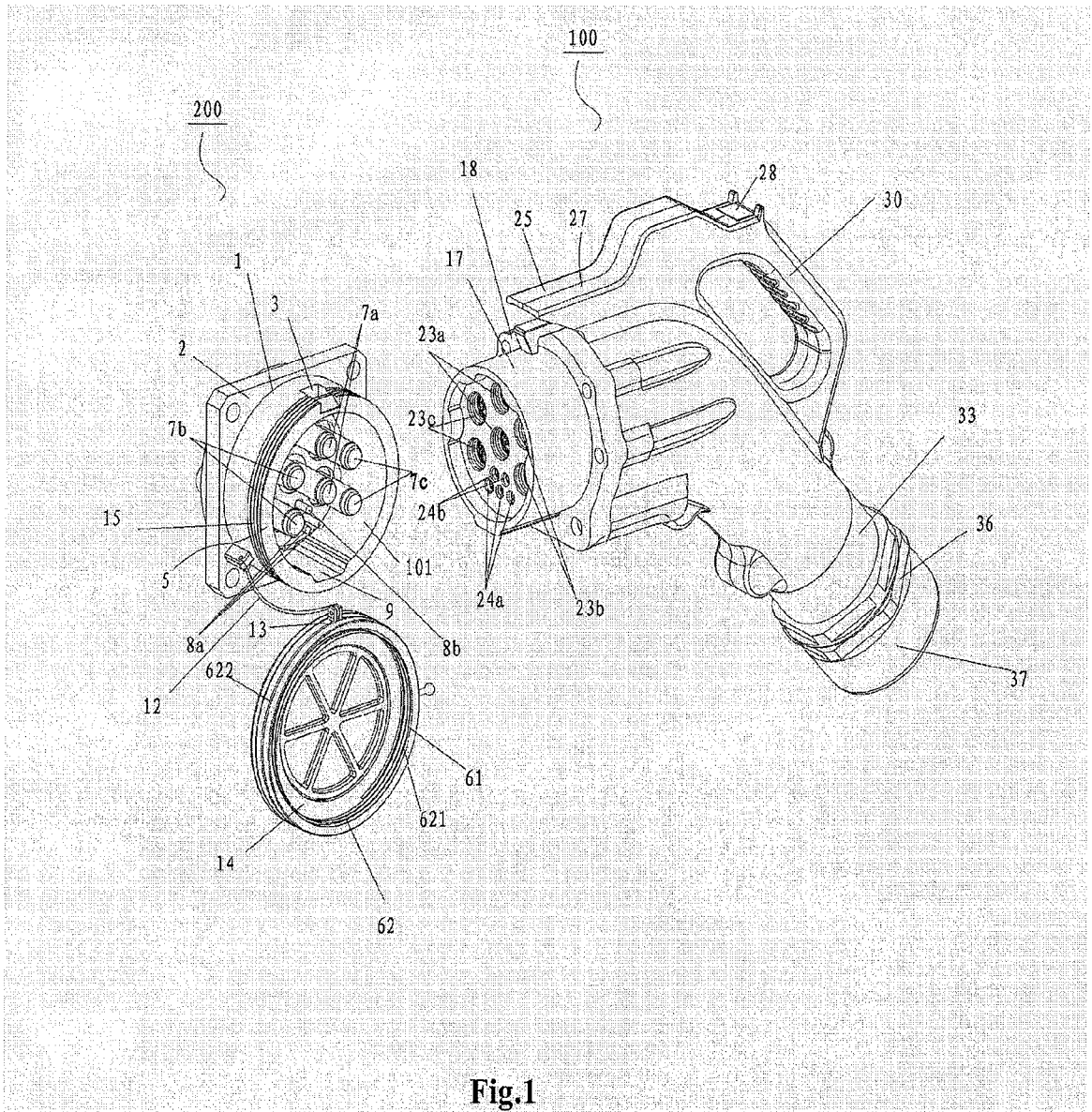

Having thus described example embodiments of the present invention in general terms, reference will now be made to the accompanying drawings, which are not necessarily drawn to scale, and wherein:

FIG. 1 is a schematic perspective view of a charging device according to an example embodiment of the present invention.

Figure 2:
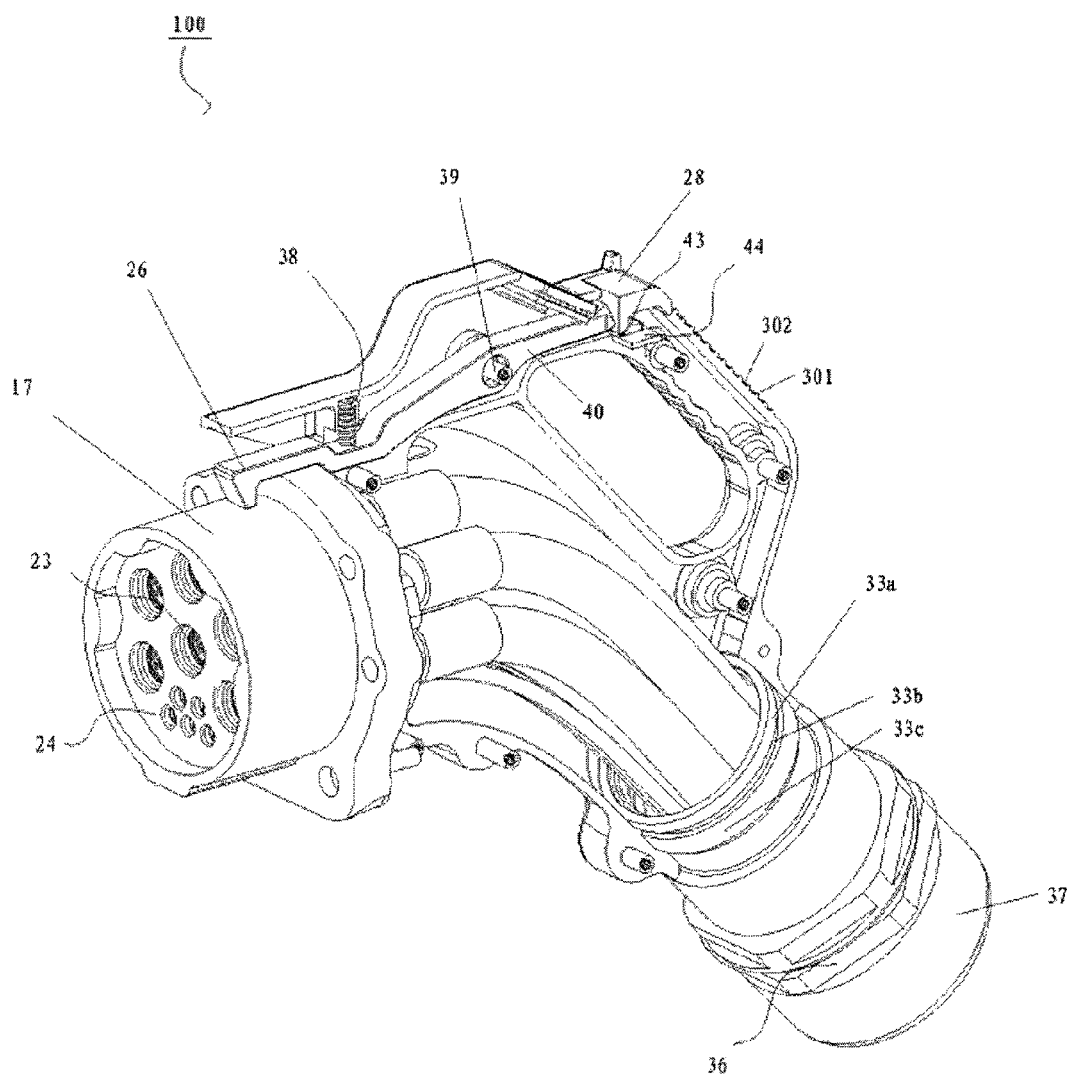

FIG. 2 is a partially sectional perspective view of a charging gun of a charging device according to an example embodiment of the present invention.

Figure 3:
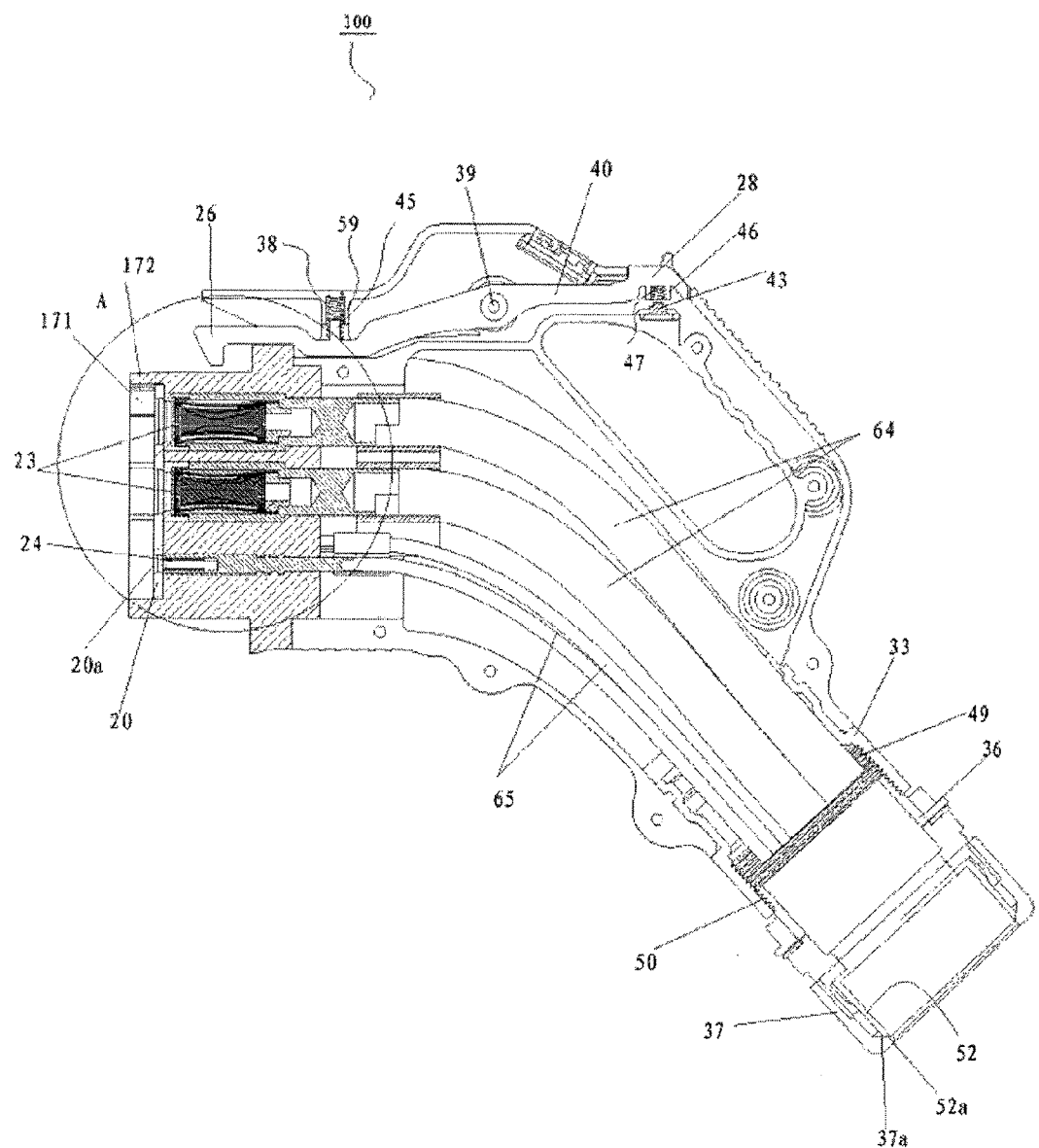

FIG. 3 is a sectional view of a charging base and a charging gun when the charging device stays in a charging process according to an example embodiment of the present invention.

Figure 4:
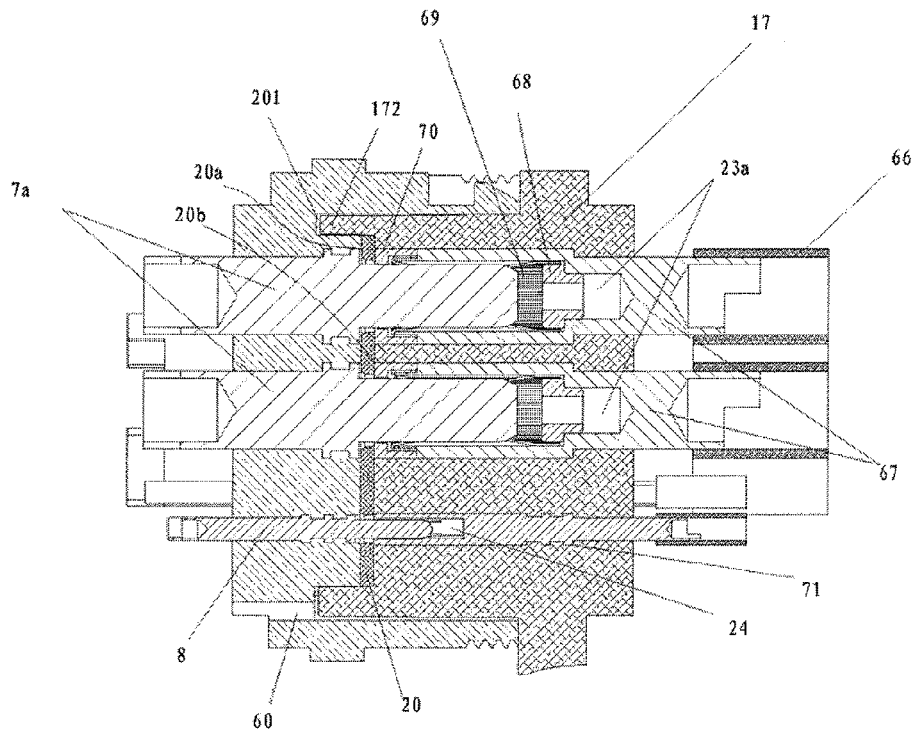

FIG. 4 is an enlarged view of a part A indicated in FIG. 3.

Figure 5:
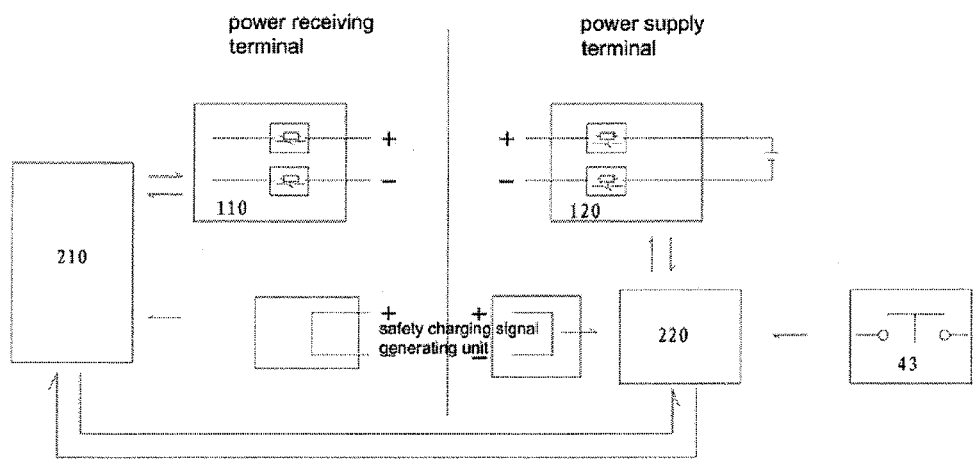

FIG. 5 is a control circuit diagram of a charging device according to an example embodiment of the present invention.

DETAILED DESCRIPTION

The present invention now will be described more fully with reference to the accompanying drawings, in which some, but not all embodiments of the invention are shown. This invention may be embodied in many different forms and should not be construed as limited to the embodiments set forth; rather, these example embodiments are provided so that this disclosure will be thorough and complete, and will fully convey the scope of the invention to those skilled in the art. Like numbers refer to like elements throughout.

In the following, the charging device for the electrically-drivable vehicle according to an example embodiment of the present invention will be described in detail taking the electric vehicles as an example. After reading the disclosed specific example embodiments of the present invention following, a person normally skilled in the art can apply the charging device to any kind or type of an electrically-drivable vehicle, such as a hybrid-power vehicle, an electric bus or the like, thus the following is described only for illustrative purpose rather than for limitation.

In the following description, for convenience, the power-receiving base configured on the electric vehicle is used to illustrate the power-receiving connector according to an example embodiment of the present invention. The charging gun is used to illustrate the power-supply connector according to an example embodiment of the present invention. However, after reading the specification of the present invention, it is obvious for a person normally skilled in the art that the structure of the power-receiving connector may be exchanged with the structure of the power-supply connector. For example, the terminal-accommodating-chamber configured on the power-supply connector may be exchanged with the terminal configured on the power-receiving connector, without departing from the scope of the present invention.

The present invention will be described below in detail through the specific example embodiments and the figures. FIG. 1 is a schematic perspective view of a charging device according to an example embodiment of the present invention. FIG. 2 is a partially sectional perspective view of a charging gun of a charging device according to an example embodiment of the present invention. FIG. 5 is a control circuit diagram of a charging device according to an example embodiment of the present invention.

As shown in FIG. 1, according to one example embodiment, the charging device may comprise a power-supply connector 100 (charging gun) configured on the power-supply end which may be a charging terminal or a charging-terminal-accommodating chamber; a power-receiving connector 200 configured on the power-receiving end which may be the other of the charging terminal or the charging-terminal-accommodating chamber; a safety-charging-signal-generating unit (as shown in FIG. 5) configured in the charging device; a CAN (Controlled Area Network) control module receiving a safety-charging signal generated by the safety-charging-signal-generating unit. The charging device is configured to be chargeable to the electrically-drivable vehicle when the charging terminal and the charging-terminal-accommodating chamber are connected to each other; the power-supply connector 100 and the power-receiving connector 200 are engaged with the CAN module detecting the safety-charging signal.

According to one example embodiment of the present invention, the charging gun 100 may be formed by an insulating seat 17, a first shell 25 connected with the insulating seat 17, and a second shell 27. The first shell 25 and the second shell 27 may be formed by the insulating materials to avoid current leakage. According to one example embodiment of the present invention, the insulating seat 17 may be connected with the first shell 25 and the second shell 27 through a metal flange 18. The metal flange 18 may have a plurality of internally threaded holes. And the first shell 25 may be connected with the second shell 27 through a bolt. A metal column with internal thread hole may be embedded into the second shell 27. According to an alternative example embodiment of the present invention, the first shell 25 and the second shell 27 may be buckled to each other.

The charging gun 100 may further comprise the first shell 25 pivotably accommodated in the charging gun; a buckling member 40 (see FIGS. 2 and 3) in the hollow chamber formed by the second shell 27; a conductive terminal-accommodating-chamber 23 formed in the insulating seat 17; a signal terminal-accommodating-chamber 24; and an indicator showing the charging status (not shown).

As shown in FIGS. 2 and 3, the end of the charging gun may comprise an adapter sleeve 33; a transition joint 36 connected with the adapter sleeve 33; and a bushing 37 connected with the transition joint 36. A groove 33b and a bump 33c of the adapter sleeve 33 may be matched with a corresponding groove and a corresponding bump of the first shell 25 and a second shell 27 of the charging gun. Threads 49 may be matched with threads 50 at an end of the transition joint 36; the other end of the transition joint 36 may be matched with the bushing 37. A rubber sleeve 52 formed with an inclining portion may be installed in the bushing 37. When the bushing 37 may be tightened inwardly, an inclining surface 52a of the rubber sleeve 52 may be pushed by an inclining surface 37a of the bushing 37, which may cause a radial shrinkage of the rubber sleeve 52, thus tightly fitting with an outer surface of a charging cable wrapped by the rubber sleeve 52. Under the friction and the radial pressure, the cable may be locked to avoid the swinging which may pull the terminal to cause the loosing at the engaging point of the charging cable with the terminal.

Further, a protrusion 301 and a groove 302 may be formed on the outer surface of a handle 30 of the charging gun 100, which can avoid slipping during operation. In addition, a protrusion and a groove may also be formed on an inner surface of the handle 30 of the charging gun 100, which can avoid the slippage.

Further referring to FIG. 1, the conductive terminal-accommodating-chamber 23 may be formed on the center of the insulating seat 17; the signal terminal-accommodating-chamber 24 may be formed at a lower part of the insulating seat 17 in cross section. Each of the conductive terminal-accommodating-chamber 23 and the signal terminal-accommodating-chamber 24 separately may have matching terminals to be connected with conductive terminals 7 and signal terminals 8 formed in the charging seat 200, the connecting state being shown in FIG. 3. As shown in FIG. 3, a groove 171 may be formed at an end of the insulating seat 17. The conductive terminal-accommodating-chamber 23 and the signal terminal-accommodating-chamber 24 may be formed respectively adjoining a bottom portion of the groove 171.

Through embedding a plurality of matching terminals to the insulating body, the conductive terminal-accommodating-chamber 23 and the signal terminal-accommodating-chamber 24 may be formed; simultaneously, the matching terminals may be fixed to the insulating seat by injection moulding, which can avoid the matching terminals disengaging from the insulating seat 17.

When the conductive terminal-accommodating-chamber 23 is engaged with the conductive terminal 7 formed in the charging base 200, the conductive terminal-accommodating-chamber 23 may be used to conduct high current. In the charging device of FIG. 1, considering the high current for charging the electric vehicles, two grounding-terminal-accommodating chambers 23a, two positive-conductive-terminal-accommodating chambers 23b and two negative-conductive-terminal-accommodating chambers 23c may be formed respectively in the insulating seat 17. Correspondingly, two grounding terminals 7a, two positive terminals 7b and two negative terminals 7c may be formed in a hollow chamber 101. However, depending on the charging current, the quantity of the conductive terminals and the conductive terminal-accommodating-chambers may be varied. For example, it may have only one conductive terminal and one corresponding conductive terminal-accommodating-chamber separately. Considering the safety, the grounding-terminal-accommodating chamber 23a may be protruding more outwardly than two positive-conductive-terminal-accommodating chambers 23b and two negative-conductive-terminal-accommodating chambers 23c. Thus when the charging gun 100 is inserted into the charging base 200, the grounding terminal 7a may be first conducted with the grounding-terminal-accommodating chamber 23a. Simultaneously, when drawing the gun, the grounding terminal 7a may be separated from the grounding-terminal-accommodating chamber 23a earlier than the other four terminals, which can provide the security for subsequent high-current charging.

As shown in FIG. 1, the signal terminal-accommodating-chamber 24 may be configured at the lower part of the conductive terminal-accommodating-chamber 23. The signal terminal accommodation 24 comprises five such signal terminal-accommodating-chambers. Three of them at the bottom may be CAN terminal-accommodating-chambers 24a, the other two may be safety signal terminal-accommodating-chambers 24b. A female terminal formed by moulding in the safety signal terminal-accommodating-chamber 24 may be short connected at the power-supply end, then after the safety signal terminal 8b is inserted successfully at last, the two safety signal terminals 8b may be short connected. Therefore, a safety-charging signal of the electric-vehicle end may be generated. Then the safety signal terminal 8b may supply the safety-charging signal to the CAN control module of the electric-vehicle end, and the safety signal terminal-accommodating-chamber 24b may supply the safety-control signal to the first CAN control unit 210 and 220 of the charging gun 100 end (as shown in FIG. 5). Correspondingly, five signal terminals 8 may be formed at the lower part of the conductive terminal 7 and in the hollow chamber 101 of the charging base 200. The arrangement of the signal terminal 8 corresponds to the arrangement of above signal terminal-accommodating-chamber 24 and may be smoothly joined with the signal terminal-accommodating-chamber 24.

According to one example embodiment of the present invention, two safety-signal terminals 8b may be longer in length than that of the CAN terminal. During engaging, two safety-signal terminals 8b may be contacted earlier than the CAN terminal. In the disengaging process of drawing out the gun, the safety-signal terminals may be separated later than the CAN terminal, thus providing additional safety to the charging process.

In addition, the integrated female terminal in the conductive terminal-accommodating-chamber 23 may be connected with one end of the charging cable 64; the integrated female terminal in the signal terminal-accommodating-chamber 24 may be connected with one end of the charging cable 65, so the conductive current and the signal may be conducted respectively. Specifically, the charging cable 64 and the signal cable 65 may be separately fixed to one end of the conductive terminal-accommodating-chamber 23 and one end of the signal terminal-accommodating-chamber 24 through a pyrocondensation pipe 66 configured at back of the insulating seat 17, as shown in FIG. 4. FIG. 4 shows an enlarged view of part A shown in FIG. 3, in which the conductive terminal 7 and the signal terminal 8 may be inserted respectively into the conductive terminal-accommodating-chamber 23 and the signal terminal-accommodating-chamber 24.

In FIG. 4, a conductive column 67 may be configured in the conductive terminal-accommodating-chamber 24. The conductive column 67 may be integrated to the conductive terminal-accommodating-chamber 24 in the moulding process. A boring hole may be formed separately in each of the two ends of the conductive column 67, and may be used to contain a flange connecter 68 and the charging cable. A conductive line spring 69 may be configured closely between the flange connector 68 and the conductive column 67. The conductive line spring 69 may be deformable. When the conductive column 67 may be inserted into the conductive terminal-accommodating-chamber 23, the conductive line spring 69 may be closely fitted with the conductive terminal 7. When a fastening sleeve 70 may be set against the conductive column 67, the second end of the conductive line spring 69 may be blocked in the gap between the sidewalls of the fastening sleeve 70 and the conductive column 67, then the conductive line spring 69 may be fixed. When the conductive line spring 69 is failed, the conductive line spring 69 may be removed and replaced by removing the fastening sleeve 70. Similarly, the signal terminal 7 may have the similar structure as described above to engage with the signal terminal-accommodating-chamber 24. Alternatively, the signal terminal may have a buckle structure to buckle to the signal terminal-accommodating-chamber 24, as shown in FIG. 4. To avoid the female terminal in the signal terminal-accommodating-chamber 24 from disengaging after moulding, a fixed groove 71 may be formed on the wall of the signal terminal-accommodating-chamber 24; a protrusion may be formed in the female terminal accordingly. Then through the engagement of the groove-protrusion, the female terminal may be formed fixedly to the insulating seat 17.

In the engagement status as shown in FIG. 4, an insulating ring 20 may be configured between the joint surfaces of charging base 200 and the insulating seat 17 of the charging gun 100. The surface 20a of the insulating ring 20 may be attached to the surface 6 of the insulating base 1 of the charging port; the surface 20b of the insulating ring 20 may be attached with the base surface of the insulating seat 17 for sealing. The liquid that may enter into the charging port base accidentally may be discharged through an outlet port 60, which may avoid the accident caused by liquid conduction.

In addition, corresponding to the groove 171 of the insulating seat 17 of the charging gun 100, a ring groove 201 may be configured at the bottom of the hollow chamber 101 of the charging base 200. The ring groove 201 may contain a flange 172 of the insulating seat 17 during charging, which may be tightly fitted with the insulating seat 17, as shown in FIG. 4.

Further, an inserting guide groove 9 may be formed at the lower part of the charging base 200. Correspondingly, a guide boss 61 may be formed at the lower part of the insulating seat 17 of the charging gun 100. When the insulating seat 17 of the charging gun 100 may be inserted into the hollow chamber 101 of the charging base 200, the guide boss 61 may be directed by the inserting guide groove 9 to enter into the hollow chamber 101 smoothly.

Below, the structure of the charging base 200 will be described in detail. According to FIG. 1, the charging base 200 may comprise a fixed seat 2, and a cylindrical accommodating chamber 1 configured on the front surface of the fixed seat 2. A water-proof cover 62 connected by a chain link 12 may also be formed in the fixed seat 2. The water-proof cover 62 may comprise a shell 621, a guide ring 13 freely rotated around the shell ring groove 622, and a sealing ring 14 inside the shell 621. During charging, the water-proof cover 62 may be connected with the charging base 200 by a chain link 12 to avoid the shell 621 from detaching. In non-charging state, threads 15 of the charging base 200 may be screwed with threads 61 of the water-proof 62; the sealing ring 14 may be attached to a surface 5 of the charging base 200 for sealing. A locking groove 3 may be formed in the upper part of the cylindrical accommodating chamber 1. The locking groove 3 may be used to buckle to the buckling member 40 formed in the charging gun 100, thus in the process of inserting the gun, the buckle fit between the buckling member 40 and the locking groove 3 can take effect as fixing, which can avoid the charging gun 100 detaching from the charging base 200 during charging. In addition, the safety-signal terminal 8b formed in the hollow chamber 101 of the cylindrical accommodating chamber 1 of the charging base 200 may be shorter in length than that of the CAN terminal 8a, and the grounding terminal 7a may be longer in length than those of the other conductive terminals. During inserting, the grounding terminals 7a may be contacted with the matching grounding-terminal-accommodating chamber 23a earlier than other terminals for providing additional protection.

The charging device further may comprise a charging lock unit. When the charging gun 100 may be inserted to the charging base 200, the charging lock unit may be used to lock them. According to one example embodiment of the present invention, the charging lock unit may comprise a locking groove 3 configured on the charging base 200, and a buckling member 40 configured on the charging gun 100. The buckling member 40 may be pivotably fixed on the first shell 25 and the second shell 27 and may have a first end 26 and a second end 28. The first end 26 may be buckled to the locking groove 3. A micro switch 43 may be connected in series to the second end 28 of the buckling member 40. When the second end 28 of the buckling member 40 is pressed, the micro switch 43 may be engaged and triggers a stopping signal to the CAN control module, consequently the charging circuit of the electric power drivable vehicle may be disengaged and a first relay module 110 and a second relay module 120 may be disengaged.

To be specific, as shown in FIG. 2, the buckling member 40 may be fixed with the first shell 25 and the second shell 27, and may rotate certain angle along a pin shaft 39. When the buckling member 40 remains in the locking status with the engagement of the charging gun 100 and the charging base 200, the first end 26 may be fitted with the locking groove 3, the micro switch 43 which is provided on the first insulating shell 25 and the second shell 27 and contacted with the bottom of the second end 28 of the buckling member 40 may be disengaged. When the second end 28 is pressed, the buckling member 40 may be disengaged, the first end 26 may be detached from the locking groove 3. At this time, the micro switch 43 may be engaged and may generate a control signal to trigger an instruction to terminate power charging to the second CAN control unit 220 which may be provided on the power supply side and detects the signal continuously, and terminates the second relay module 120. At the same time, the second CAN module 220 communicates with the first CAN module 210 through the engagement of the CAN terminal 8a with the CAN terminal-accommodating-chamber 24a, and a power termination instruction may be generated in the power receiving side, and the first relay module 110 may be disengaged, as shown in FIG. 5. An electric arc can be avoided when the high current may be cut off by accident, which can protect the operators.

The buckling member 40 can rotate a certain angle around the pin shaft 39. When the second end 28 is pressed, the second end 28 moves downwardly to press a spring 47 located in a column protrusion 46, and the spring 47 pushes the micro switch 43 provided on a circuit board 44 to engage, so that an engagement signal is triggered to the second CAN control unit 220.

A return protrusion 45 may be formed on the front end of a pivot shaft 39 of the buckling member 40. A return spring 38 may be nested on the return protrusion 45 and accommodated in a column protrusion 59 which may have an accommodation groove. When unfastening the second end 28 of the buckling member 40, due to the return force of the return spring 38 of the column protrusion 59 and the spring 47, the buckling member 40 return to the original position. At this time, the micro switch 43 may be disengaged to trigger a disengaging signal to the second CAN control unit 220, and the power may be cut off.

Further, the charging device may comprise a first relay module 110 configured on the power-supply end, and a second relay module 120 configured on the power-receiving end. The first relay module 110 and the second relay module 120 may be conducted separately when the first control module 210 and the second control module 220 receive the charging signals, accordingly, the charging circuit may be conducted and the electric power vehicle may be charged correspondingly.

Based on specific description of the charging base 200 and the charging gun 100 mentioned hereinabove, a control logic for the charging device of the electric power vehicles according to one example embodiment of the present invention will be described hereinafter according to FIG. 5. FIG. 5 shows a control circuit diagram of the charging device according to one example embodiment of the present invention.

According to one example embodiment of the present invention, besides the security provided by the mechanical matching between the conductive terminal 7 and the conductive terminal-accommodating-chamber 23, the engagements of the signal terminals 8 (the CAN terminal 8a and the safety-signal terminal 8b) with the signal terminal-accommodating-chambers 24 (the CAN terminal-accommodating-chamber 24a and the safety signal terminal-accommodating-chamber 24b) provide a safety-charging-signal-generating unit. To be specific, the safety-signal terminal 8b may be shorter in length than that of the CAN terminal 8a, so only after the CAN terminal 8a may be inserted completely into the CAN terminal-accommodating-chamber 24a and the communication of the first CAN control unit 210 and the second CAN control unit 220 is started, the engagement of the safety-signal terminal 8b and the safety signal terminal-accommodating-chamber 24b may trigger the communication signals and send to the first CAN control unit 210 and the second CAN control unit 220 respectively. The first CAN control unit 210 and the second CAN control unit 220 may be interacted respectively with the power and the first relay module 110, the second relay module 120, and control the whole charging process. The disengagement and the engagement of the first relay module 110 and the second relay module 120 greatly reduce the arc, so accidental personal injury may be reduced greatly. Therefore, the mechanical structure may be combined with the CAN control module according to one example embodiment of the present invention, which provides duo-security during the charging process.

In addition, the control circuit may receive the engaging and the disengaging signals from the micro switch. Considering the safety issue, when the operator pushes the second end 28 of the buckling member 40 and triggers the micro switch 43 to generate disengaging or engaging signal, the second CAN control unit 220 will communicates with the first CAN control unit 210 (if the CAN terminal may be conductive at this time). And the first CAN control unit 210 and the second CAN control unit 220 will control their own control circuit respectively; the power source, the first relay module 110 and the second relay module 120 may be cut off; which can protect the safety of the operator at maximum.

In the following, the operation of the charging device according to one example embodiment of the present invention will be described.

In the charging process by inserting the gun, the safety signal terminal-accommodating-chamber 24b may have the electric contact later than the CAN terminal-accommodating-chamber 24a. In the gun-drawing-out process, the safety signal terminal-accommodating-chamber 24b may be detached earlier than the CAN terminal-accommodating-chamber 24b. During charging, when contacting with the safety-signal terminal 8b, the safety signal terminal-accommodating-chamber 24b sends signals to the first CAN control unit 210 and the second CAN control unit 220; the first CAN control unit 210 and the second CAN control unit 220 may be used to control the first relay module 110 and the second relay module 120 to engage, then the electric power vehicle may be charged. When drawing the gun out and the safety signal terminal-accommodating-chamber 24b may be detached from the safety-signal terminal 8b, the circuit may be cut off, and the signals may be triggered to the first CAN control unit 210 and the second CAN control unit 220 respectively. The first CAN control unit 210 and the second CAN control unit 220 may be used to control the first relay module 110 and the second relay module 120 to disengage, which may obviate the electric arc to protect safety of the operator. From above, when detaching, the signal terminal may always be cut off earlier than that of the charging terminal. Thus the signal terminal always triggers the signal earlier than the conductive terminal and may be used to cut off the power source timely, and the electric arc may be eliminated to avoid the safety accident.

During engaging, if the first CAN control unit 210 and the second CAN control unit 220 do not receive the ready status signals of the safety-signal terminal 8b and the safety signal terminal-accommodating-chamber 24b, the first CAN control unit 210 and the second CAN control unit 220 will not engage the first relay module 110 and the second relay module 120, which will obviate the possibility of accidental injury.

In addition, when the first end 26 of the buckling member 40 does not buckle to the locking groove 3 completely by the charging lock unit, and the safety-signal terminal 8b may not contact with the safety signal accommodating chamber 24b, the engaging signal will not be generated and the first relay module 110 and the second relay module 120 will not occur, then the electric arc will not happen accidentally.

Further, during the whole charging period, the micro switch 43 may be in the normal open status, when pushing the second end 28 of the buckling member 40 and triggering the micro switch 43, the circuit may be engaged, then a signal may be triggered to ask the first CAN control unit 210 and the second CAN control unit 220 to cut off the charging power, the first relay module 110 and the second relay module 120 at the same time.

When detaching, the safety-signal terminal 8b may be cut off earlier than the CAN terminal 8a, when the signals may be triggered to the first CAN control unit 210 and the second CAN control unit 220. Having received such signals, the first CAN control unit 210 and the second CAN control unit 220 will cut off the power timely. Then the accidental security problem caused by discharging phenomena will be avoided.

In the following, from Table 1, each control module status is described in the whole charging process and the draw-gun process.

TABLE 1 control process of the charging and draw-gun of the charging device

| No. | Status | CAN control module | Safety-signal terminal | Charging status |
|---|---|---|---|---|
| 1 | not inserting | N | N/Y | N |
| 2 | inserting | N | N | N |
| 3 | inserted status 1 | Y | N | N |
| 4 | inserted status 2 | Y | Y | Y |
| 5 | Gun to be drawn | Y | N | N |
| 6 | Gun drawn | N | N | N |

N shows the charging status is negative, the Y shows the status is positive. Only when all the status is Y, can both the first relay module 110 and the second relay module 120 be engaged and start to charge. For other status, the first relay module 110 and the second relay module 120 will be disengaged, which will protect the safety of the operator maximally.

In Table 1, when the charging gun 100 is not engaged with the charging base 200 completely, the first CAN control unit 210 and the second CAN control unit 220 may both be not in the working status, and the safety-signal terminal 8b does not generate the charging triggering signal. Even the safety-signal terminal 8b generates charging signal accidentally, the charging device does not enter into the charging status. Then the charging security of the charging device may be ensured.

In the process of inserting the charging gun 100 into the charging base, because the safety-signal terminal 8b is not engaged with the short circuit safety signal terminal-accommodating-chamber 24b. At this time, the safety-signal terminal does not trigger the charging signal. Thus, the charging device does not enter into the charging status.

After inserting, when the CAN terminal 8a is engaged with the CAN terminal-accommodating-chamber 24a whereas the safety-signal terminal 8b is not engaged with the safety terminal-accommodating-chamber 24b, the charging device may be in the inserted status 1, but now the charging device does not enter into the charging status.

When the safety-signal terminal 8b is engaged with the safety signal terminal-accommodating-chamber 24b, the charging device is in the inserted status 2; now the charging signal is triggered by the first CAN control unit 210, the second CAN control unit 220 and the safety-signal terminal. Thus, the charging device enters into the charging status.

After the charging process is finished, draw-gun operation may be needed. At this time, the safety-signal terminal 8b may be separated from the safety signal terminal-accommodating-chamber 24 first, but the CAN terminal 8a does not disengaged with the CAN terminal-accommodating-chamber 24a completely, so the first CAN control unit 210 and the second CAN control unit 220 still may operate to cut off the first relay module 110 and the second relay module 120. However, the charging device has stopped the charging process.

Lastly, after the gun is drawn out or withdrawn completely, the first CAN control unit 210 and the second CAN control unit 220 stop operating, and the safety-signal terminal stops triggering a charging signal. At this time, the charging device stops charging completely.

Thus, it can be seen, in above charging process, only when the CAN control module is in the working status and after the safety-signal terminal triggers the charging signal, may the charging device be used for charging the vehicle. Thus, the safety of the charging device may be enhanced greatly in the charging process, and the operation of the first relay module 110 and the second relay module 120 may also reduce or eliminate the electric arc.

Many modifications and other embodiments set forth herein will come to mind to one skilled in the art to which these example embodiments pertain having the benefit of the teachings presented in the foregoing descriptions and the associated drawings. Therefore, it is to be understood that the embodiments are not to be limited to the specific ones disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions other than those explicitly described above are also contemplated as may be set forth in some of the appended claims. Although specific terms are employed herein, they are used in a generic and descriptive sense only and not for purposes of limitation.

That which is claimed:

1. A charging device for an electrically-drivable vehicle, comprising:
   a power-supply connector provided on a power-supply end and including a charging terminal or a charging-terminal-accommodating chamber;
   a power-receiving connector provided on a power-receiving end and including the other of the charging terminal or the charging-terminal-accommodating chamber;
   a safety-charging-signal-generating unit provided in the charging device;
   a CAN (Controlled Area Network) control module configured to receive a safety-charging signal generated by the safety-charging-signal-generating unit;
   wherein the charging device is configured to be chargeable to the electrically-drivable vehicle when the charging terminal and the charging-terminal-accommodating chamber are connected to each other, the power-supply connector and the power-receiving connector being engaged with the CAN module configured to detect the safety-charging signal.

2. The charging device according to claim 1, wherein the power-supply connector further comprises:
   an insulating seat with the charging terminal or the charging-terminal-accommodating chamber being formed therein; and
   a shell of the power-supply connector connected with the insulating seat.

3. The charging device according to claim 2, wherein the power-receiving connector is formed with a hollow chamber with the other of the charging terminal or the charging-terminal-accommodating chamber being configured therein.

4. The charging device according to claim 3, wherein the CAN control module comprises:
   a first CAN control unit configured on the power-receiving end; and
   a second CAN control unit configured on the power-supply end.

5. The charging device according to claim 4, wherein the safety-charging-signal-generating unit further comprises:
   a signal terminal configured on the power-supply connector or the power-receiving connector; and
   a signal terminal-accommodating-chamber configured on the other of the power-supply connector or the power-receiving connector.

6. The charging device according to claim 5, the signal terminal further comprises:
   a CAN terminal; and
   a safety-signal terminal;
   wherein the signal terminal-accommodating-chamber further comprises:
   a CAN terminal-accommodating-chamber; and
   a safety signal terminal-accommodating-chamber;
   wherein, when the CAN terminal engages with the CAN terminal-accommodating-chamber, the first CAN control unit communicates with the second CAN control unit; and when the safety-signal terminal engages with the safety signal terminal-accommodating-chamber, the safety-signal terminal triggers a charging signal to the first CAN control unit and the second CAN control unit to charge the vehicle.

7. The charging device according to claim 6, wherein a length of the safety-signal terminal is shorter than that of the CAN terminal.

8. The charging device according to claim 6, further comprising:
   a first relay module configured on the power-supply end; and
   a second relay module configured on the power-receiving end;
   wherein the first relay module and the second relay module are conducted when the charging signal is received by a respective one of the first CAN control unit and the second CAN control unit, thus conducting a charging circuit to charge the vehicle.

9. The charging device according to claim 8, further comprising:
   a charging lock unit to lock the power-supply connector and the power-receiving connector when inserted.

10. The charging device according to claim 9, wherein the charging lock unit comprises:
    a locking groove configured on the power-receiving connector; and
    a buckling member configured on the power-supply connector, wherein the buckling member has a first end and a second end is pivotably fixed on the power-supply connector with the first end capable of buckling to the locking groove.

11. The charging device according to claim 1, wherein a micro switch is connected in series to the second end of the buckling member, and when the second end of the buckling member is pressed, the micro switch is engaged triggering a stopping signal to the CAN control module to disengage the charging circuit of the electric power drivable vehicle and disengage the first relay module and the second relay module.

12. The charging device according to claim 1, wherein the power-receiving connector further comprises:
    a sealing cover threadedly connected to the power-receiving connector to seal an open end of the power-receiving connector.

13. The charging device according to claim 1, wherein a guiding groove is formed at a lower part of the power-receiving connector with a guiding bump being formed at a lower part of the power-supply connector, so that the power-supply connector and the power-receiving connector are guided by the engagement of the guiding groove and the guiding bump during inserting.

* * * * *